(12) United States Patent
Mori et al.

(10) Patent No.: US 8,867,699 B2
(45) Date of Patent: Oct. 21, 2014

(54) RADIOGRAPHIC DEVICE

(75) Inventors: Kazuhiro Mori, Otsu (JP); Shingo Baba, Kyoto (JP); Naoki Hasegawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 651 days.

(21) Appl. No.: 13/222,318

(22) Filed: Aug. 31, 2011

(65) Prior Publication Data

US 2013/0051514 A1     Feb. 28, 2013

(51) Int. Cl.
*G01N 23/00* (2006.01)
*A61B 6/00* (2006.01)
*G01N 23/04* (2006.01)
*A61B 6/06* (2006.01)

(52) U.S. Cl.
CPC .............. *G01N 23/04* (2013.01); *A61B 6/5235* (2013.01); *A61B 6/06* (2013.01); *G01N 2223/401* (2013.01)
USPC .............................................. 378/2; 382/128

(58) Field of Classification Search
CPC ............ G01N 2223/401; G01N 23/04; G01N 23/046; A61B 6/5235
USPC .............................................. 378/4; 382/128
See application file for complete search history.

(56) References Cited

U.S. PATENT DOCUMENTS

| | | | | | |
|---|---|---|---|---|---|
| 6,157,700 | A | * | 12/2000 | Sako | 378/98.12 |
| 6,173,086 | B1 | * | 1/2001 | Hara | 382/276 |
| 7,336,811 | B2 | * | 2/2008 | Takeo | 382/132 |
| 7,424,138 | B2 | * | 9/2008 | Takagi | 382/128 |
| 7,463,712 | B2 | * | 12/2008 | Zhu et al. | 378/7 |

FOREIGN PATENT DOCUMENTS

JP          2002-325755 A       11/2002

* cited by examiner

*Primary Examiner* — Hoon Song
*Assistant Examiner* — Danielle Fox
(74) *Attorney, Agent, or Firm* — McDermott Will & Emery LLP

(57) ABSTRACT

A radiographic device includes grid frequency component eliminating processing means for eliminating a grid frequency component from an original image detected by a radiation detecting device; wherein said means includes a BPF and an HPF for producing a band-pass grid image and a high-pass grid image from an original image through band-pass and high-pass extraction; a subtracting device for taking the difference between these two grid images; an LPF for producing a difference grid image comprising the grid frequency components not completely extracted by the band-pass, through performing a low-pass processed on the difference image in a direction that is parallel to the grid pattern; an adding device for producing a band-pass+difference grid image by adding the difference grid image to the band-pass grid image; and a subtracting device for subtracting the band-pass+difference grid image from the original image.

2 Claims, 9 Drawing Sheets

FIG. 5
(a) (See Step S1.)
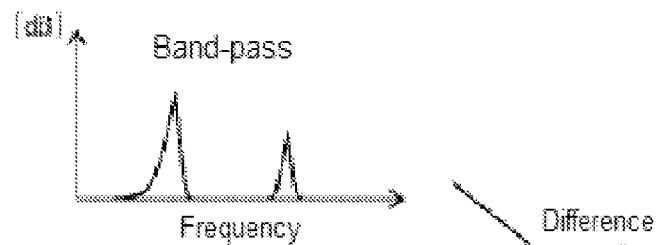
(b) (See Step S2.)
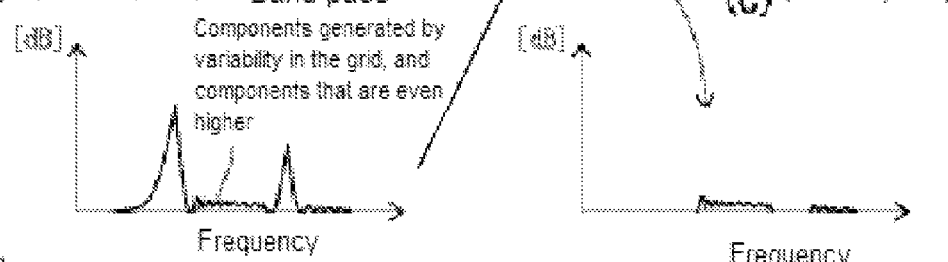
(c) (See Step S4.)
(d) (See Step S3-2.)
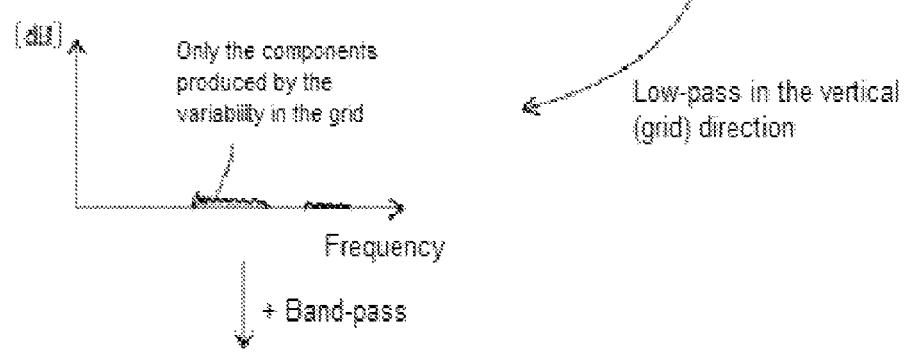
+ Band-pass
(e) (See Step S4.)
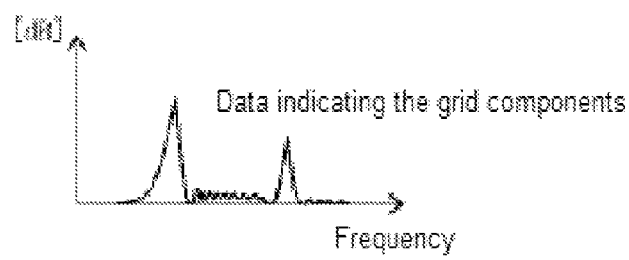

FIG. 14
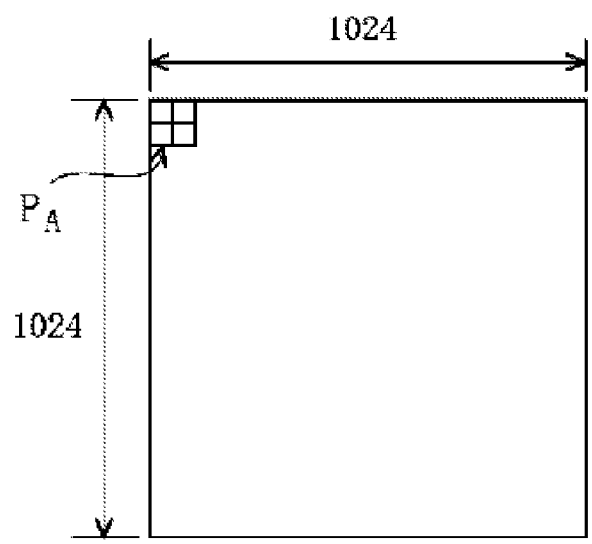
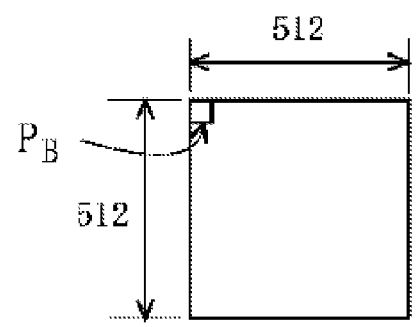

RADIOGRAPHIC DEVICE

CROSS REFERENCE TO RELATED APPLICATION

This application is based on Japanese Patent Application No. 2009-094315 filed Apr. 8, 2009, which is incorporated herein by reference. This application was published Oct. 28, 2010 as JP 2010-240259.

FIELD OF TECHNOLOGY

The present invention relates to a radiographic diagnosing device using a planar radiation detecting device.

BACKGROUND OF THE INVENTION

The explanation will use an example of an x-ray imaging device as the radiographic device.

In an x-ray imaging device, x-rays are emitted from an x-ray tube towards an object to be examined, and those x-rays that pass through the object to be examined are detected, and x-ray imaging is performed by producing an x-ray image based on the detected x-rays. When the x-rays pass through the object being examined, scattered rays are produced through collisions of the x-rays with the object being examined, and blurring of the image results from the scattered rays.

Given this, in order to eliminate the scattered rays, which have been scattered by the object being examined, in x-ray imaging devices a grid is used wherein substances having high x-ray absorbency and substances having low x-ray absorbency are lined up in parallel alternating at fixed intervals, where a moire pattern is produced in the image that is produced by the x-ray detecting device due to the differences in the spatial frequency possessed by the grid (the array spacing) and the spatial sampling period (the detection pixel spacing) of the x-ray detecting device.

Because of this, conventionally a variety of measures have been put in place in order to eliminate or reduce the moire pattern in this type of imaging:

(1) The use of a grid having the same frequency characteristics as the x-ray detecting device, so as to not produce the moire pattern is one of these known measures;

(2) There is also the cancellation of the moire pattern through moving the grid during x-ray exposure;

(3) Along with this, in order to eliminate the high-frequency components such as the moire pattern (which may also be termed the "grid pattern") that comprises a grid frequency component (shown in FIG. 5($e$)), such as appears in an x-ray emission image (="original image," such as shown in FIG. 6) when using a grid, conventionally [A] the application of low-pass filtering (LPF) in a direction that cuts across the grid pattern perpendicularly (that is, in the direction that is perpendicular to the grid elements) has been performed, or [B] after extracting high-frequency components that include the grid frequency component, by performing high-pass filtering (HPF) in a direction that cuts across the grid pattern perpendicularly, the high-frequency components are subtracted from the original image, to eliminate the grid high-frequency components, or the like, are known as examples of such processes.

Furthermore, [C] a grid image (a band-pass grid image) is produced by performing band-pass extraction of the grid high-frequency components from an original image by passing it through a band-pass filter (BPF) (as shown in FIG. 5($a$)). An image processing technology has also been proposed wherein the band-pass grid image is subtracted from the original image in order to exclude the grid-frequency components from the original image.

Describing this in specifics, when a Fourier transform is performed on the original image to calculate the spectrum intensities, if, as illustrated in FIG. 12, the binning size in the horizontal direction is x1 pixels, then the peaks of the grid frequency will appear in the vicinity of ½x and 1x the Nyquist frequency Nq (as illustrated in FIG. 13($a$)). Similarly, in the case of an image where in the binning size in the horizontal direction is x2, then a grid frequency peak will appear in the vicinity of 1x the Nyquist frequency Nq (as shown in FIG. 13($b$)).

When it comes to the frequencies at which the peaks occur, if the array spacing of the grid is defined as 1g and the detecting element spacing thereof is 1p, then if 1g<1p, the moire pattern pitch 1m will be:

$$1m = 1p \times 1g/(1p - n \times 1g).$$

Here $n=0, 1, 2, \ldots$, and if 1g is no more than 2×1p then n will be 1, but if greater than 2x and no more than 3x, then n will be 2, and thus the frequency fm corresponding to the grid frequency peak will produced as $fm=(1p-n\times 1g)/1p\times 1g$ (where the second harmonic is twice this).

Note that the peak on the right side, i.e., the second peak, shown in FIG. 5($a$) corresponds to the second harmonic of the peak of the grid frequency on the left side (where the frequency where the peak appears=fm).

The band-pass extraction described above is a technique for detecting these peaks to extract the applicable frequencies from the original image. However, there still remains the problem of residual moire pattern, as described below, that exists in frequency domains other than the peaks due to variability in the grid, and the like.

When it comes to this, as can be understood from FIG. 8, which relates to the example of embodiment set forth below, and from the explanation thereof, vertical lines will remain throughout FIG. 8. As illustrated in FIG. 8, under the conventional technology it is only possible to eliminate the grid frequency component to this degree, where there is residual moire pattern in x-ray illumination images from which the grid images (the band-pass grid images) have been subtracted.

Further, an example of this can be found in Japanese Unexamined Patent Application Publication 2002-325755.

Here, in the case (1) wherein a grid having the same frequency characteristics as the x-ray detecting device is used, this should not be effective unless the matching is strict, and thus extremely high levels of positional accuracy and manufacturing accuracy for the grids are required, which cannot be produced inexpensively. For example, even if such grids could be produced, if there were a variation in the SID (the distance between the x-ray source and the x-ray detecting device), then the match between the frequency characteristics would be disrupted, where even a minute variation in the SID will produce a frequency difference, making the moire pattern visible.

Moreover, in the case (2) wherein the grid is moved during the x-ray emission, a separate moving mechanism or device is required, and thus there are problems in that this not only leads to an increase in overall size of the equipment, but also leads to increases in manufacturing costs.

Furthermore, when (3) image processing is performed so as to eliminate the high-frequency components that include also the grid frequency, the pattern that is produced in the original image by the grid cannot be extracted and cut out by only the [C] band-pass, for example, and thus there will be the problem of a residual pattern in the original image from which the grid image has been subtracted.

Given this, in contemplation of the above, the object of the present invention is to provide an improved x-ray imaging device able to resolve the residual moire pattern that is due to differences between the grid spatial frequency characteristics and the x-ray detecting device spatial frequency characteristics, able to do so through image processing through an extremely simple structure, without problems in terms of cost.

SUMMARY OF THE INVENTION

As the cumulative result of a variety of investigations into solutions for the problem set forth above, the inventors in the present application discovered that it is possible to create a grid image through high-pass extraction (a high-pass grid image) separate from the band-pass extraction grid image (the band-pass grid image), and that taking the difference between these two grid images (a difference grid image) makes it possible to produce the moire pattern component that cannot be extracted completely by the grid image through band-pass extraction, and further discovered that subtracting this difference grid image added to this band-pass grid image (a band-pass+difference grid image) from the original image makes it possible to eliminate the moire image from the original image without residual (band-pass+high-pass processed image), resulting in the present invention.

A radiographic device according to the present invention, able to achieve the object set forth above is:

(1) A radiographic device having a radiation generating device; a scattered ray removing grid, disposed so that radiation passing through an examination object will be incident therein, wherein portions with high radiation absorbency and portions with low radiation absorbency are arrayed alternatingly in parallel; a radiation detecting device, disposed so that radiation that has passed through the scattered ray removing grid will be incident therein, wherein the spatial sampling period of the vertical and/or horizontal direction that cuts across the grid pattern is equal to that of the grid pattern; grid frequency component eliminating processing means for performing a process for eliminating a grid frequency component from an original image that has been detected and acquired by the radiation detecting device through the scattered ray removing grid; wherein:

the grid frequency component eliminating processing means includes a band-pass filter for performing a process for producing a band-pass grid image through band-pass extraction from the original image by performing a band-pass process on the original image in a direction that cuts across the grid pattern perpendicularly; a high-pass filter for performing a process for producing a high-pass grid image through high-pass extraction from the original image by performing a high-pass process on the original image in a direction that cuts across the grid pattern perpendicularly, to pass high frequency components of the grid pattern that are extracted by the high-pass process by the high-pass filter; first differencing means for taking a difference between the band-pass grid image and the high-pass grid image; a low-pass filter for performing a process for producing a difference grid image from the grid frequency components that were not extracted completely in the band-pass through performing a low-pass process, on the difference image, in a direction that is parallel to the grid pattern; adding means for producing separately a band-pass+difference grid image by adding the difference grid image to the band-pass grid image; and second differencing means for subtracting the band-pass+difference grid image from the original image.

Additionally, an invention according to the present invention is (2) a method for eliminating a grid frequency component from an original image that has been detected and acquired by a radiation detecting device, through a scattered radiation grid, in a radiographic device comprising: a radiation generating device; a scattered ray removing grid, disposed so that radiation passing through an examination object is incident therein, wherein portions with high radiation absorbency and portions with low radiation absorbency are arrayed alternatingly in parallel; a radiation detecting device, disposed so that radiation that has passed through the scattered ray removing grid is incident therein, wherein the spatial sampling period of the vertical and/or horizontal direction that cuts across the grid pattern is equal to that of the grid pattern; having a process for producing a band-pass grid image through band-pass extraction from the original image by a band-pass filter performing a band-pass process on the original image in a direction that cuts across the grid pattern perpendicularly; a process for producing a high-pass grid image through high-pass extraction from the original image by performing a high-pass process on the original image, by allowing passage of high frequency components of the grid pattern that are extracted by the high-pass process by the band-pass filter, which is a high-pass filter, in a direction that cuts across the grid pattern perpendicularly; a process for obtaining a difference between the band-pass grid image and the high-pass grid image, and for producing a difference grid image from the grid frequency components that were not extracted completely in the band-pass through performing a tow-pass process, by a low-pass filter, on the difference image, in a direction that is parallel to the grid pattern; a process for producing separately a band-pass+difference grid image by adding the difference grid image to the band-pass grid image; and a process for obtaining a band-pass+high-pass processed image by subtracting the band-pass+difference grid image from the original image.

Given the present invention, a grid image (a high-pass grid image) is produced through high-pass extraction, separate from the band-pass extraction grid image (the band-pass grid image), and taking the difference between these two grid images makes it possible to produce the moire pattern that could not be extracted completely by the grid image from the band-pass extraction (the difference grid image).

Moreover, it is possible to produce a so-called "composite grid image" (a band-pass+difference grid image) by adding, to the grid image (the band-pass grid image) from band-pass extraction, the image components of the moire pattern (the difference grid image) that could not be extracted completely by a the band-pass, extracted in this way, and to perform a process of extracting this band-pass+difference grid image from the original image to eliminate the moire pattern from the original image without residual (the band-pass+high-pass processed image).

That is, the present invention makes it possible to provide a clear processed image wherein the residual of the moire image in the original image wherein the grid image was subtracted, which could not be eliminated conventionally, is eliminated.

The present invention makes it possible to eliminate the grid frequency components, without residual, while maintaining the high-frequency components from the original image.

The present invention makes it possible to eliminate the grid frequency components, without residual, while maintaining the resolution of the original image.

In this way the present invention is able to provide an improved x-ray imaging device able to resolve the residual moire pattern that is due to differences between the grid spatial frequency characteristics and the x-ray detecting device spatial frequency characteristics, able to do so through image processing through an extremely simple structure, without problems in terms of cost.

Note that the "vertical low-pass process" (or "grid-direction tow-pass process") in the present Specification refers to performing a low-pass process through a low-pass filter in a direction that is parallel to the grid pattern.

When it comes to the "binning" or "binning size" in the present Specification, "binning" refers to handling a number of pixels as a group. For example, as illustrated in FIG. 14(a), handling a total of four pixels PA (2×2 in the vertical and horizontal directions) together as a single pixel PB corresponds to 2×2 binning Combining into a single pixel causes, for example, an x-ray image comprising 1024×1024 (vertical×horizontal) pixels, as illustrated in FIG. 14(a) to form an x-ray image comprising 512×512 (vertical×horizontal) pixels, as illustrated in FIG. 14(b), reducing the data size to ¼.

However, when reference is made to the binning size being x1, this corresponds to 1×1 binning, meaning that, in this image, the pixels are used as-is. On the other hand, when reference is made to the binning size being x2, this corresponds to 2×2 binning, meaning that a region of a total of four adjacent pixels (vertical and horizontal) are combined together into a single larger pixel. Note that in this case the sensitivity to light is four times as high (four pixels' worth), but the image resolution is dropped by half. FIG. 14 shows this effect as well.

In the present Specification, the Nyquist frequency Nq refers to a frequency that is one half the sampling frequency is when a given signal is sampled. At the time of sampling, a phenomenon occurs wherein the frequencies above the Nyquist frequency Nq are folded back (also known as "aliasing"), so that, at the time of reproduction, the original signal is not reproduced faithfully.

BRIEF DESCRIPTION OF THE DRAWINGS

FIGS. 5(a)-5(e) are schematic diagrams illustrating the frequency characteristics obtained in each processing step performed in the graphics processing in an example.

FIGS. 14(a) and 14(b) are schematic diagrams of an image provided in the explanation of the binning process.

DETAILED DESCRIPTION OF THE INVENTION

Examples according to the present invention are explained in detail below in reference to the drawings.

Note that in the explanation below, an example of an x-ray imaging device will be used to explain the radiographic device.

Figure 1:
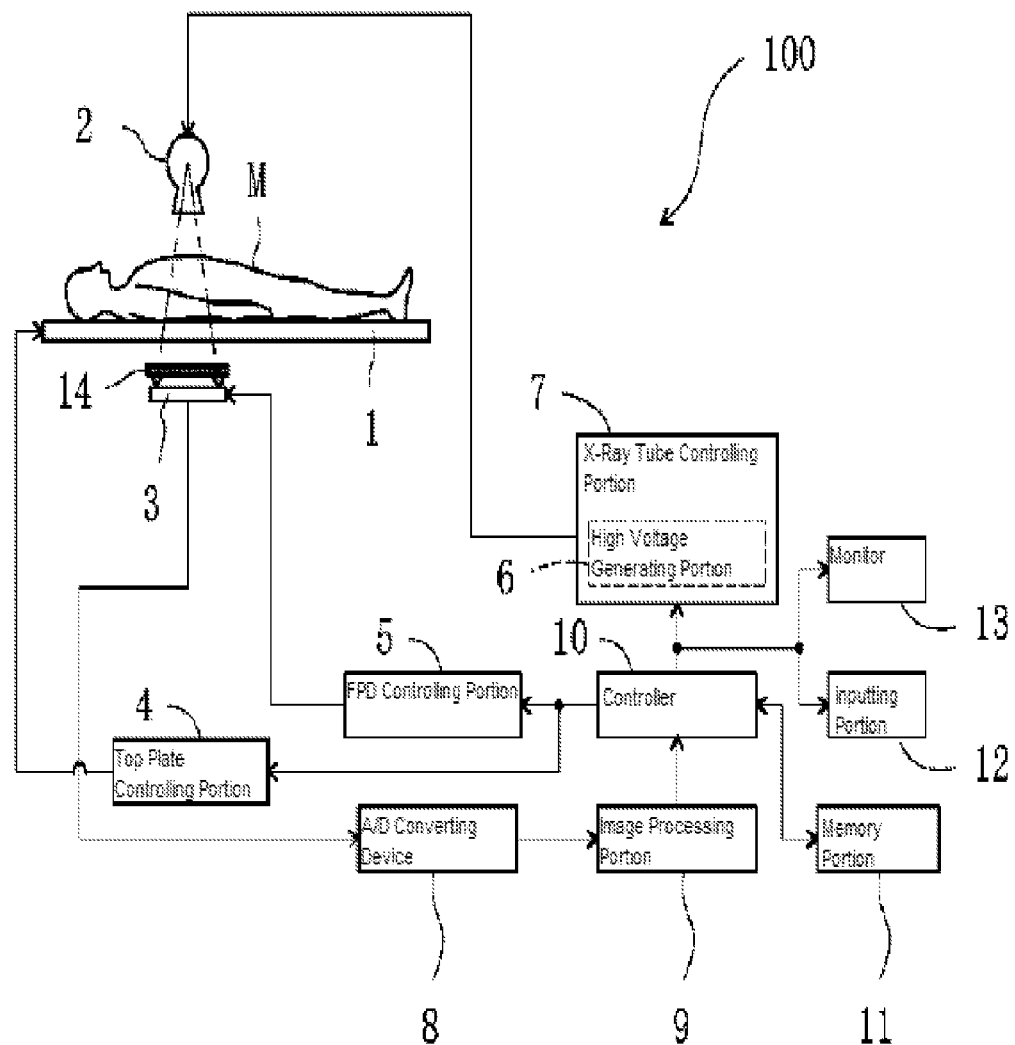
FIG. 1 is a block diagram of a radiographic device according to an example.

As illustrated in FIG. 1, an x-ray imaging device 100 includes a top plate 1 on which is placed an examination object M; an x-ray tube 2 for emitting x-rays towards the examination object M; and a flat-panel x-ray detecting device (hereinafter abbreviated "FPD") 3 for detecting the x-rays that pass through the examination object M. Note that an image intensifier or an x-ray film may be used instead of the FPD as the x-ray detecting device. The x-ray tube 2 corresponds to the x-ray emitting means in the present invention.

The x-ray imaging device further has a top plate controlling portion 4 for controlling vertical and horizontal motion of the top plate 1; an FPD controlling portion 5 for controlling scanning of the FPD 3; an x-ray tube controlling portion 7 having a high voltage generating portion 6 for producing a tube voltage and a tube current for the x-ray tube 2; an A/D converting device 8 for digitizing the x-ray detection signal that is an electric charge signal from the FPD 3; an image processing portion 9 for performing a variety of processes based on the x-ray detection signal outputted from the A/D converting device 8; a controller 110 for overall control of each of the structural portions; a memory portion 11 for storing processed images, and the like; an inputting portion 12 by which the operator performs inputs and set up; a monitor 13 for displaying processed images, and the like; and so forth.

The top plate controlling portion 4 performs control such as moving the top plate 1 in the horizontal direction so that the examination object M will be contained within the imaging location, setting the examination object M to a specific location by moving upward or downward, rotating, and moving horizontally, performing imaging while moving horizontally, retracting from the imaging position through horizontal movement after the imaging has been completed, and the like.

The FPD controlling portion 5 performs control relating to scanning, such as moving the FPD 3 horizontally, or moving rotationally around the axis of the examination object M.

The high voltage generating portion 6 generates the tube voltage and tube current for causing the x-rays to be emitted and applies them to the x-ray tube 2, and the x-ray tube controlling portion 7 performs control regarding scanning through moving the x-ray tube 2 horizontally or moving it rotationally around the axis of the examination object M, performs control so as to set the field of view of the collimator (not shown) on the x-ray tube 2 side, and the like.

Note that when scanning the x-ray tube 2 or the FPD 3, both are moved while the x-ray tube 2 and the FPD 3 face each other, so as to enable the x-rays emitted by the x-ray tube 2 to be detected by the FPD 3.

The A/D converting device 8 converts the electric charge signal that is outputted from the FPD 3 from analog into digital, and outputs a digitized x-ray detection signal. The controller 10 is structured from a central processing unit (CPU), and the like, where the memory portion 11 is structured from a storage medium such as typified by, for example, a ROM (a read-only memory) or a RAM (a random-access memory), or the like.

Additionally, the inputting portion 12 is structured from a mouse, a keyboard, and/or a pointing device such as a joystick, a trackball, a touch panel, or the like. In the x-ray imaging device, the x-rays that pass through the examination object M are detected by the FPD 3, and imaging of the examination object M is performed through performing image processing, by the image processing portion 9, based on the detected x-rays.

Note that in order to eliminate the scattered rays, an x-ray grid 14 is provided on the incident surface side of the FPD 3. The x-ray grid 14 is structured from, for example, lead and aluminum provided lined up in parallel alternatingly.

When the scattered rays are incident into the x-ray grid 14, they move forward to the lead at an angle, and are thus eliminated through being absorbed by the lead.

On the other hand, when x-rays other than scattered rays are incident into the x-ray grid 14, they move forward in parallel with the aluminum or the lead, and pass through the aluminum to be incident on the FPD 3, and thus are detected. The x-ray grid 14 corresponds to the scattered ray removing grid in the present invention.

Figure 2:
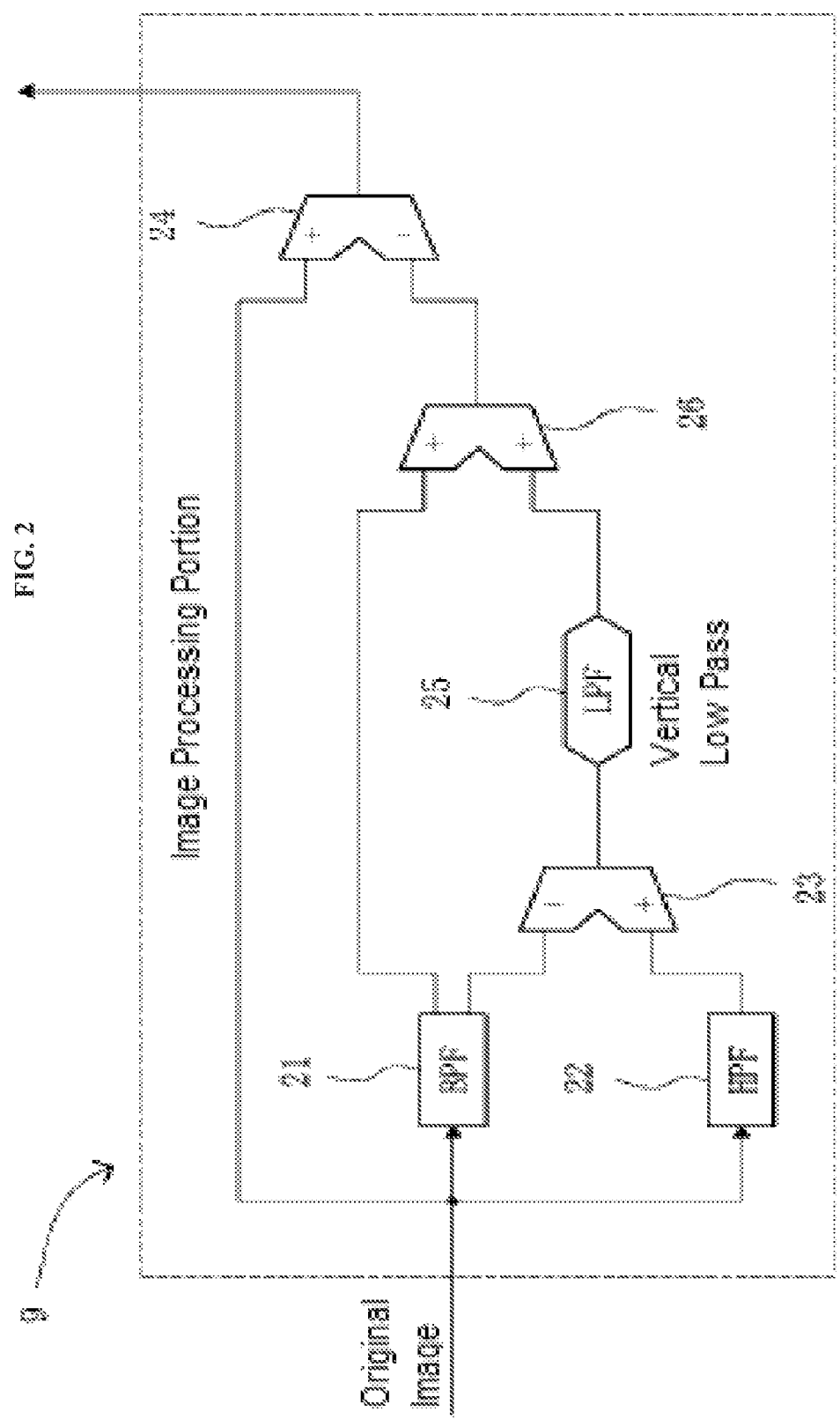
FIG. 2 is a block diagram illustrating a specific configuration of a graphic processing portion.

As illustrated in FIG. 2, the image processing portion 9, which corresponds to the grid frequency component eliminating processing means in the present invention, is structured through the provision of a band-pass filter 21 (notated as "BPF" in FIG. 2), a high-pass filter 22 (notated as "HPF" in FIG. 2), subtracting devices 23 and 24 that correspond to the differencing means, and an adding device 26 that corresponds to the adding means, and a low-pass filter 25 for performing a vertical low-pass process, described below. The connection relationships between the various structural elements are as illustrated in FIG. 2. Note that in the explanation below, the explanation will be given omitting the structures pertaining to the binning process and the steps for the binning process.

The steps in the image processing are explained again in later stages while referencing FIG. 3, FIG. 4, and FIG. 5. Note that each of the frequency characteristic diagrams of (a) through (e) illustrated in FIG. 5 shows the level (decibels) of the frequency components extracted, or the like, through the fitter processes, and the like, described below.

The low-pass filter 25 for performing the aforementioned vertical low-pass process is required when performing the low-pass process (the vertical low-pass process) using the low-pass filter in the direction that is parallel to the grid pattern.

Figure 13:
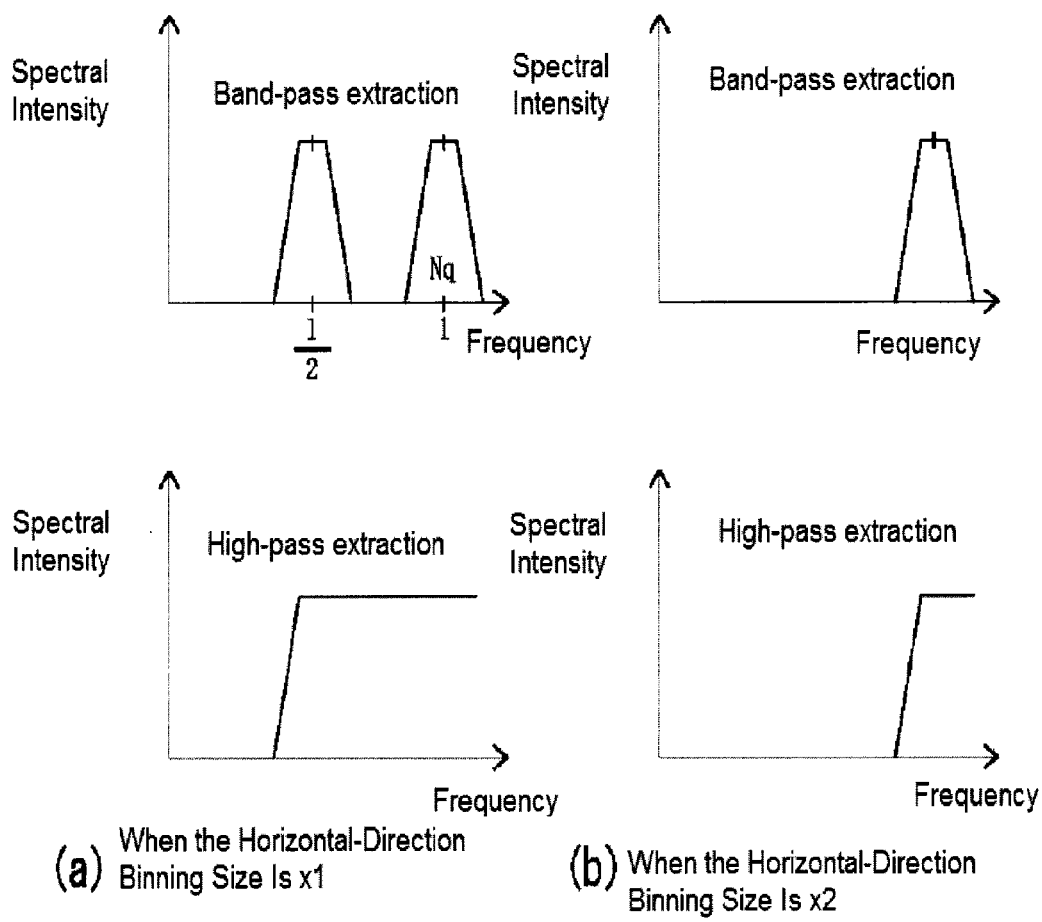
FIGS. 13(a) and 13(b) are schematic diagrams of an image provided in the explanation of binning size, band-pass extraction, and high-pass extraction.

The band-pass filter, in the same manner as earlier, is that which produces the grid image (the band-pass grid image) by performing a band-pass extraction of the grid frequency components from the original image by performing a band-pass process (a BPF process), using the band-pass fitter 21, in a direction that cuts across the grid pattern perpendicularly, on the original image that was detected and acquired by the FPD 3. (See FIG. 5(*a*) and FIG. 13 for an image of the band-pass extraction.)

The high-pass fitter, in the same manner as earlier, is that which produces the grid image (the high-pass grid image) by performing a high-pass extraction of high-frequency components that include the grid frequency components from the original image by performing a high-pass process (an HPF process), using the high-pass filter 24, in a direction that cuts across the grid pattern perpendicularly, on the original image that was detected and acquired by the FPD 3. (See FIG. 5(*b*) and FIG. 13 for an image of the band-pass extraction.) When it comes to the blocking frequency of the high-pass filter 22, it is the:

$$fm=(1p-n\times 1g/1p\times 1g),$$

which is the frequency corresponding to the peak of the grid frequency that is extracted by the band-pass process by the band-pass filter 21 described above. Here n=0, 1, . . . ; 1g is the grid layout spacing, where if 1g<1p or 1g is no more than 2×1p, then n=1, but if between 2× and no more than 3×, then n=2.

The subtracting device 23, the adding device 26, and the subtracting device 24, respectively, take the difference between the band-pass grid image and the high-pass grid image (shown in FIG. 5(*c*)), produce an image (a band-pass+difference grid image, shown in FIG. 5(*d*)) Wherein an image wherein a vertical low-pass process has been added to this difference (a difference grid image, shown in FIG. 5(*d*)), and produces an image (a band-pass+high-pass processed image) wherein the band-pass+difference grid image has been subtracted from the original image.

The series of image processes by the image processing portion 9 are explained next in reference to the block diagram of the image processing portion in FIG. 2, the system structure diagram in FIG. 3, the flowchart in FIG. 4, and the explanatory diagram in FIG. 5.

An overview of the image process that is performed in the present invention is explained first.

In the present invention, two different grid images are produced from the original image: a grid image through band-pass extraction (a band-pass grid image, shown in FIG. 5(*a*)), and a grid image through high-pass extraction (a high-pass grid image, shown in FIG. 5(*b*)).

Here, as illustrated in FIG. 5(*b*), the moire pattern having the grid frequency components that are not completely extracted by the band-pass are extracted by the high-pass, and thus the difference between the two grid images (shown in FIG. 5(*c*)) is used to extract that pattern.

Note that, as can be understood from FIG. 5(*e*), the difference image that is produced is an image wherein there remains only the high-frequency components of the original image, including the components that are produced through variability in the grid and components that are higher than that. In the present invention, a low-pass process (the vertical low-pass process) through a low-pass filter 25 is applied to the difference image in a direction that is parallel to the grid pattern. (See FIG. 5(*d*).) This is because only the pattern comprising the components produced from variability in the grid, that is, having the grid frequency components that are not completely extracted by the band-pass, has vertical directionality. Passing through the vertical low-pass process causes only the pattern comprising the frequency components that are produced through variability in the grid (that are not completely extracted by the band-pass) to remain in the difference image. (See FIG. 5(*d*).) The pattern (the difference grid image) comprising the grid frequency components that are not completely extracted by the band-pass is extracted in the present invention as described above.

Following this, a so-called "composite grid image" (a band-pass+difference grid image) is produced by adding the difference grid image (shown in FIG. 5(*d*)) produced in the present invention to the band-pass grid image from the band-pass extraction (shown in FIG. 5(*a*)). (See FIG. 5(*e*).) This serves as data showing the grid frequency components comprising also the components that arise due to variability in the grid.

Lastly, the band-pass+difference grid image (shown in FIG. 5(d)) is subtracted from the original image, making it possible to eliminate the moire pattern from the original image without leaving residual (the band-pass high-pass processed image).

In this way, the present invention makes it possible to perform a moire pattern eliminating process that does not leave behind a moire pattern having grid frequency components, while all other frequency components remain.

Note that the detailed flow of the image processes according to the present form of embodiment will be explained below following the sequence of the individual steps.

(Preliminary Step) Original Image Acquisition

X-rays are emitted from the x-ray tube 2 towards the examination object M, and the x-rays that pass through the examination object are detected by the flat panel-type x-ray detecting device (FPD) 3. Prior to incidence on the FPD 3, scattered rays are eliminated through passing through the x-ray grid 14. Doing so acquires an original image wherein a grid pattern (a moire pattern) due to the x-ray grid 14 is present.

(Step S1) Band-Pass Filter Process (See FIG. 5(a).)

As illustrated in FIG. 5(a), the grid image (the band-pass grid image) is produced by performing a band-pass extraction of the grid frequency components from the original image by the band-pass filter 21 performing a band-pass process (a BPF process), in a direction that cuts across the grid pattern perpendicularly, on the original image that was detected and acquired by the FPD 3. Here the passing band in the band-pass filter 21 is set to a band in the vicinity of the frequency fm corresponding to the band at which the peak of the grid frequency, described above appears, together with the second harmonic thereof.

Note that when it comes to the individual processes that are explained below in reference to the explanatory diagrams in FIG. 5, the extractions in Step S1 and S2, illustrated in FIGS. 5(a) and (b), are performed for each pixel line in the direction perpendicular to the grid, and aside from these, the steps wherein each of the subsequent steps are performed to ultimately perform a correction that eliminates the moire pattern from the original pattern without residual, that is, the steps to produce the image after image processing (the band-pass+ high-pass processed image) are all processes that are performed for each of the aforementioned pixel lines, except for the vertical low-pass process illustrated in FIG. 5(d).

(Step S2) High-Pass Filter Process (See FIG. 5(b).)

As with Step S1, and as illustrated in FIG. 5(b), the grid image (the high-pass grid image) is produced by passing and extracting the high-frequency components, which include the grid frequency components, from the original image by the high-pass filter 22 performing a high-pass process (an HPF process), in a direction that cuts across the grid pattern perpendicularly, on the original image that was detected and acquired by the FPD. When it comes to the blocking frequency of the high-pass filter 22, it is the:

$$fm=(1p-n\times1g/1p\times1g),$$

which is the frequency corresponding to the peak of the grid frequency that is extracted by the band-pass process by the band-pass filter 21 described above. Here n=0, 1, 2, . . . ; 1g is the grid layout spacing, where if 1g<1p or 1g is no more than 2×1p, then n=1, but if between 2x and no more than 3x, then n=2.

(Step S3-1) Difference Between Images (See FIG. 5(c).)

The difference between the band-pass grid image and the high-pass grid image that have been produced is taken next by the subtracting device 23.

The vertical low-pass process is applied thereto (Step S3-2, difference grid image).

(Step S3-2) Vertical Low-Pass Process (See FIG. 5(d).)

After the difference has been taken in Step S3-1, a low-pass process (the vertical low-pass process, shown in FIG. 5(d)) is applied the difference image, in a direction that is parallel to the grid pattern. This is because only the pattern comprising the components produced from variability in the grid, that is, comprising the grid frequency components that are not completely extracted by the hand-pass, has vertical directionality. Performing the vertical low-pass process causes only the pattern of the grid (which was not completely extracted by the band-pass) to remain in the difference image. As described above, this extracts the pattern of the grid that "was not completely extracted by the band-pass" (the difference grid image).

Note that even in the step in accordance with FIG. 5(d), as with the case illustrated in FIG. 5(c), it is possible that there may be a grid frequency component that is higher than the second harmonic, albeit extremely small, in FIG. 5(c). As can be understood from FIG. 5(d), if it exists, it is at such a small level that it is essentially negligible.

(Step S4) Adding the Difference Grid Image to the Band-Pass Grid Image (See FIG. 5(e).)

Following this, the difference grid image that has been produced is added to the hand-pass grid image that has already been calculated, to produce the band-pass+difference grid image. This serves as data showing the grid frequency components comprising also the components that arise due to variability in the grid.

(Step S5) Subtracting the Band-Pass+Difference Grid Image from the Original Image After this, the band-pass+difference grid image is subtracted from the original image to produce the band-pass+ high-pass processed image that is that which is ultimately to be produced.

The band-pass+high-pass processed image produced through the various processing steps set forth above maintains the high-frequency components from the original image and eliminated reliably the grid frequency components, and thus it can be understood that the problems with so-called "residual moire patterns" is eliminated.

Based on the above, an example according to the present invention is explained in detail, in sequential order, while showing another example of an actual grid image. The structure of the radiographic device according to the present example, the control system, and system structure thereof, and the overall flow of the image processing are as described above.

FIG. 6 through 12 are an example of reference images illustrating the flow of processes performed by the image processing portion 9, corresponding to the grid frequency component eliminating processing means of the radiographic device according to the present invention. The images in FIG. 6 through 12 are images for each processing step in the image processing performed in the radiographic device according to the present example of embodiment. These are all examples of images produced when imaging a so-called "examination sample" M, and have been recorded in order to explain the individual processing steps in the image processing that is performed in the radiographic device according to the present example. Consequently, be aware that that which was produced when actually imaging this examination sample M using the radiographic device according to the present example was the image according to FIG. 12 (the band-pass+ high-pass processed image 57).

Here, when explaining each processing step in the radiographic device according to the present example, the states to which the images in FIG. 6 through 12 apply (that is, which processing steps were they recorded in) will be explained briefly.

Figure 6:
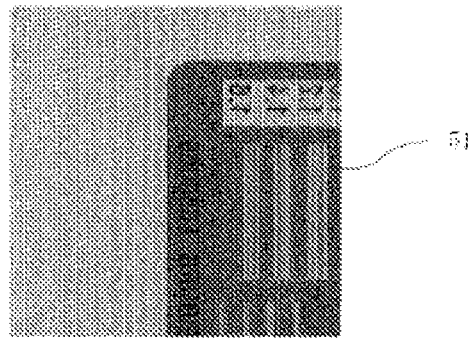
FIG. 6 is a diagram illustrating one example of the original image.

FIG. 6 shows the original image 51. That is, FIG. 6 shows the x-ray emission image itself acquired by the detection, by the FPD 3, through the examination object M and the x-ray grid 14 (that is, an image in a state wherein no image processing has been performed). It can be understood that the moire pattern due to the grid is apparent in the original image in FIG. 6.

Figure 7:
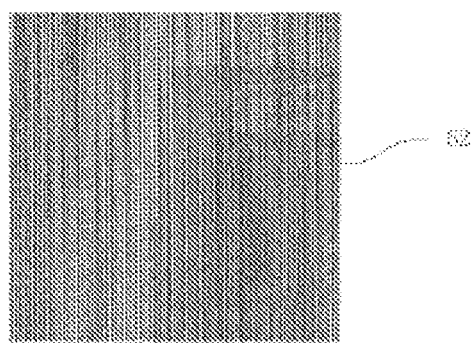
FIG. 7 is a diagram illustrating one example of a band-pass grid image.

FIG. 7 is the grid image (the band-pass grid image 52) extracted by the band-pass filter 21 from the original image S1 of FIG. 6. (See Step S1 in FIG. 5(a).)

Figure 8:
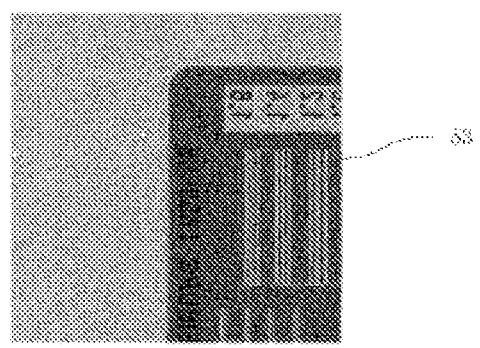
FIG. 8 is a diagram illustrating one example of a band-pass processed image.

FIG. 8 is the image (the band-pass processed image 53) wherein the band-pass grid image 52 of FIG. 7 has been subtracted from the original image of FIG. 6. It can be understood that vertical lines remain throughout this image.

As illustrated in FIG. 8, under the conventional technology it is only possible to eliminate the grid frequency component to this degree, and this there has been a problem in that there has been residual moire pattern in x-ray illumination images from which the grid images have been subtracted. As described above, the present invention solves this problem through the provision of the image processing steps described below.

Figure 9:
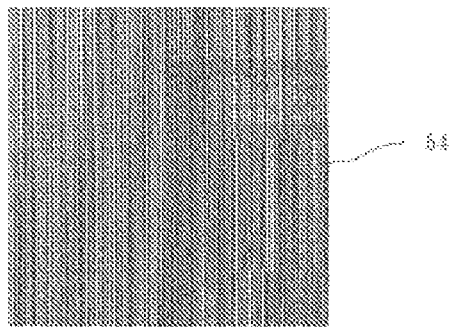
FIG. 9 is a diagram illustrating one example of a high-pass grid image.

FIG. 9 is the grid image (the high-pass grid image 54) extracted by the high-pass filter 22 from the original image 51 of FIG. 6. (See Step S2 and FIG. 5(d).)

Figure 10:
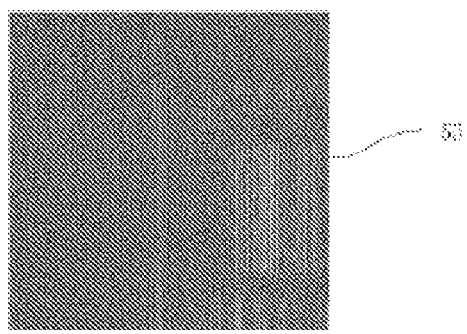
FIG. 10 is a diagram illustrating one example of a difference grid image.

FIG. 10 is the image (the difference grid image 55) wherein the vertical low-pass process has been applied to the difference between the band-pass grid image 52 of FIG. 7 and the high-pass grid image 54 of FIG. 9. (See Step S3-1, S3-2, and FIGS. 5(c) and (d).)

Figure 11:
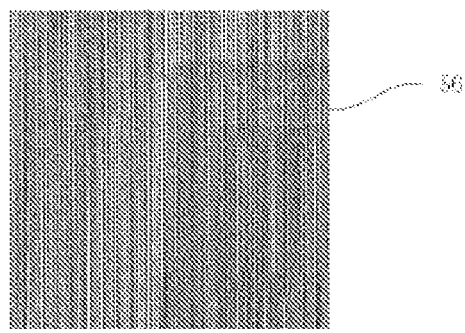
FIG. 11 is a diagram illustrating one example of a band-pass+difference grid image.

FIG. 11 is the image (the band-pass+difference grid image 56) wherein the difference grid image 55 of FIG. 10 has been added to the band-pass grid image 52 of FIG. 7. (See Step S4 and FIG. 5(e).)

Figure 12:
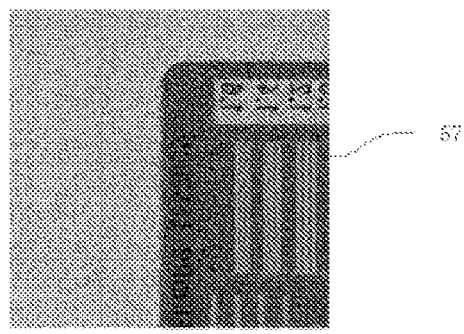
FIG. 12 is a diagram illustrating one example of a band-pass+high-pass processed image.

FIG. 12 is the result that is produced (the band-pass+high-pass processed image 57) by finally subtracting, from the original image of FIG. 6, the band-pass difference grid image 56 of FIG. 11, (See Step S5.) It can be understood that the vertical lines have disappeared in this image.

[Image Processing Steps]

Figure 3:
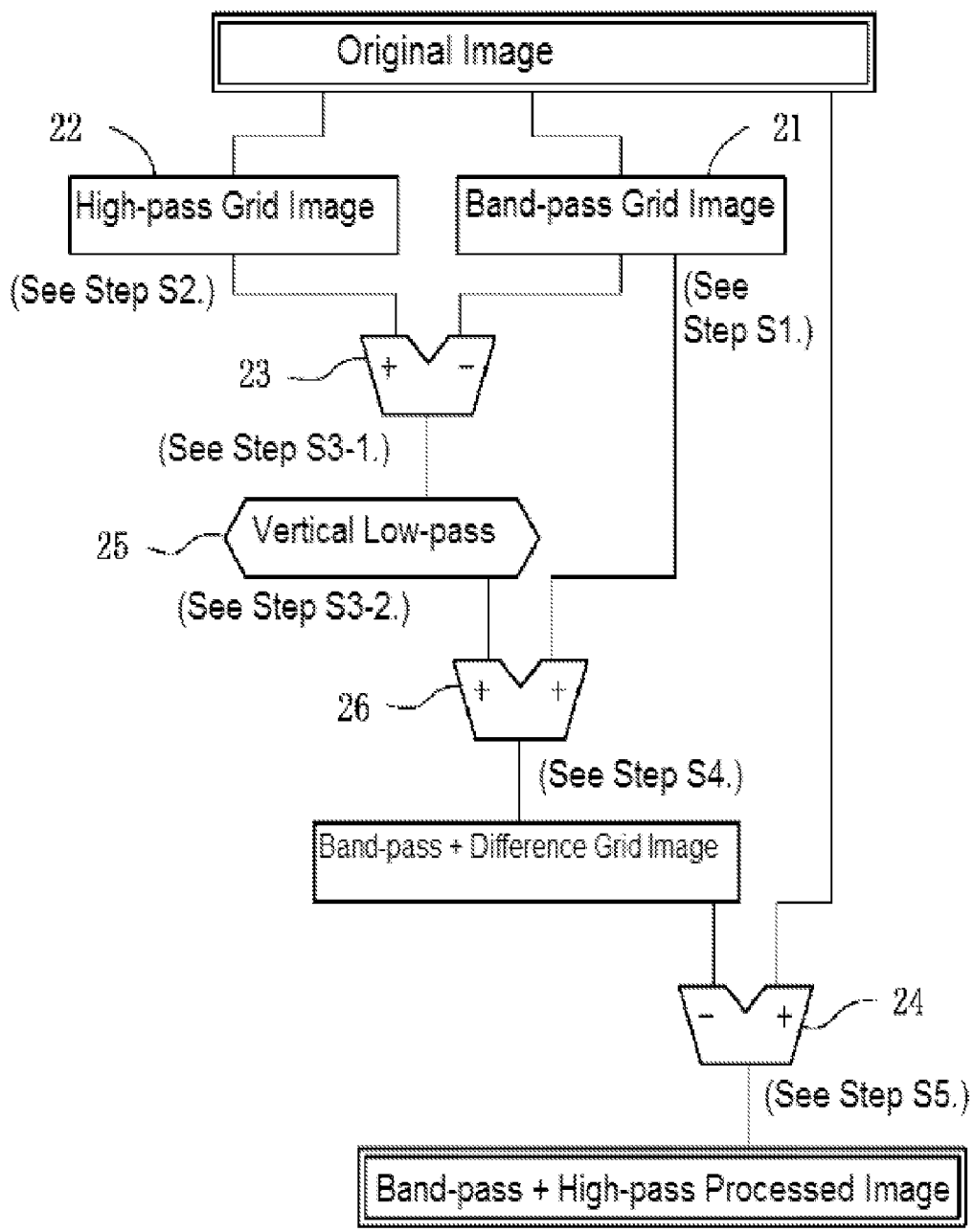
FIG. 3 is a system structure diagram illustrating each processing step performed in the graphics processing in the present form of embodiment, and a schematic of the connection relationships therebetween.
Figure 4:
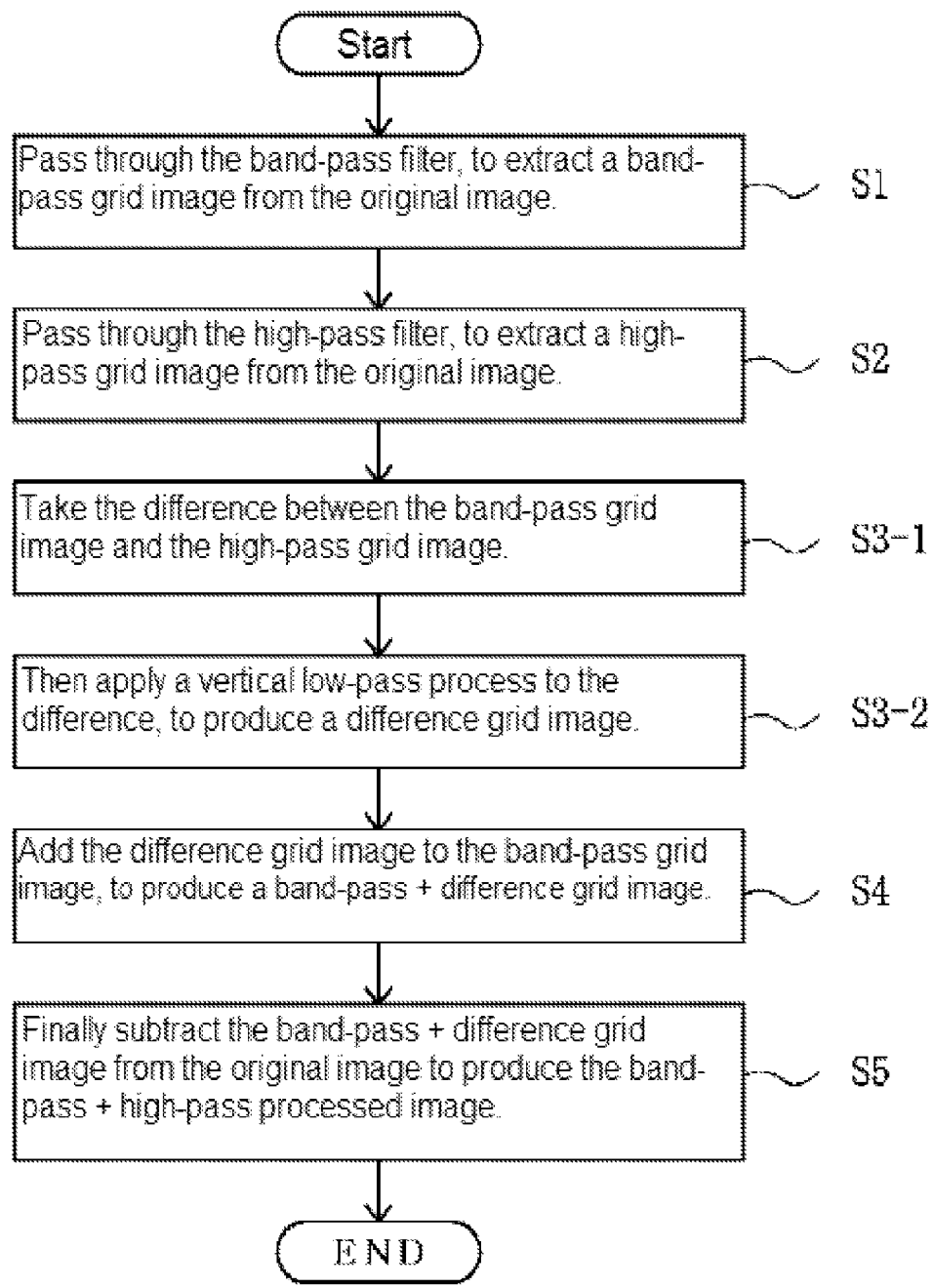
FIG. 4 is a flowchart illustrating the flow of the graphics processing in the radiographic device according to an example.

The flow of the image processing performed in the present example are explained in sequence based on FIG. 3, FIG. 4, and FIG. 5. Note that it is assumed in the explanation that the original image of FIG. 6, in which the grid pattern due to the x-ray grid 14 (the moire pattern) was projected onto the FPD 3, has been acquired.

First the grid images extracted by the band-pass filter 21 and the high-pass filter 22 front the original image 51 in FIG. 6 (the band-pass grid image 52 of FIG. 7 and the high-pass grid image 54 of FIG. 9) are produced (Step S1 and S2, shown in FIGS. 5(a) and (b).)

Following this, the vertical low-pass process is applied (Step S3-1) to the difference between the band-pass grid image 52 and the high-pass grid image 54 that have been produced, to produce the difference grid image 55 of FIG. 10, (Step S3-2, shown in FIGS. 5(c) and (d).)

Thereafter, the difference grid image 55 of FIG. 10 that has been produced is added to the band-pass grid image 52 of FIG. 7, to produce the band-pass+difference grid image 56 of FIG. 11. (Step S4, shown in FIG. 5(e).)

Then, ultimately, the band-pass+difference grid image 56 of FIG. 11 is subtracted from the original image 51 of FIG. 6, to calculate the band-pass+high-pass processed image 57 of FIG. 12. (Step S5.)

It is this band-pass+high-pass processed image 57 of FIG. 12 that is the result that is to be produced through the present example. Compared to the band-pass processed image 53 of FIG. 8, it can be seen that the vertical lines have disappeared in the band-pass+high-pass processed image 57 of FIG. 12.

Note that the present invention is not limited to the examples set forth above, but rather modified forms are possible, as described below.

(1) While in the example of an x-ray imaging device was used for explaining the radiographic device, the present invention may be applied to radiographic devices that perform radiography to produce radiographic images based on detected radiation by detecting radiation other than x-rays (γRays in the case of a PET device), such as in PET (positron emission tomography) devices, SPECT (single-photon emission CT) devices, and other ECT (emission computed tomography) devices.

(2) White in one of the examples set forth above the explanation used the radiographic device 100 illustrated in FIG. 1 as an example, the present invention may be applied also to x-ray imaging devices that are disposed on, for example, C-shaped arms. Moreover, the present invention may also be applied to x-ray CT devices.

(3) While in one of the examples set forth above the explanation was given omitting the relationship with the binning process, there is no limitation thereto, but rather the structure may be one wherein an appropriate binning process is performed.

The invention claimed is:

1. A radiographic imaging device comprising:
a radiation generating device;
a scattered ray removing grid, disposed so that radiation passing through an examination object is incident therein, wherein portions with high radiation absorbency and portions with low radiation absorbency are arrayed alternatingly in parallel;
a radiation detecting device, disposed so that radiation that passed through the scattered ray removing grid is incident therein, wherein the spatial sampling period of the vertical and/or horizontal direction that cuts across a grid pattern is equal to that of the grid pattern;
grid frequency component eliminating processer performing a process for eliminating a grid frequency component from an original image that has been detected and acquired by the radiation detecting device through the scattered ray removing grid; wherein:
the grid frequency component eliminating processer comprises:
a band-pass filter producing a band-pass grid image through band-pass extraction from the original image by performing a band-pass process on the original image in a direction that cuts across the grid pattern perpendicularly;
a high-pass filter producing a high-pass grid image through high-pass extraction from the original image by performing a high-pass process on the original image in a direction that cuts across the grid pattern perpendicularly, to pass high frequency components of the grid pattern that are extracted by the high-pass process by the high-pass filter;
a first differencing engine taking a difference between the band-pass grid image and the high-pass grid image;

a low-pass filter producing a difference grid image from the grid frequency components that were not extracted completely in the band-pass through performing a low-pass process, on the difference image, in a direction that is parallel to the grid pattern;

an adding device producing separately a band-pass+difference grid image by adding the difference grid image to the band-pass grid image; and a second differencing engine subtracting the band-pass+difference grid image from the original image.

2. A method for eliminating a grid frequency component from an original image that has been detected and acquired by a radiation detecting device, through a scattered radiation grid, in a radiographic device comprising:

a radiation generating device;

a scattered ray removing grid, disposed so that radiation passing through an examination object is incident therein, wherein portions with high radiation absorbency and portions with tow radiation absorbency are arrayed alternatingly in parallel;

a radiation detecting device, disposed so that radiation that has passed through the scattered ray removing grid is incident therein, wherein the spatial sampling period of the vertical and/or horizontal direction that cuts across a grid pattern is equal to that of the grid pattern;

said method comprising the steps of:

producing a band-pass grid image through band-pass extraction from the original image by a band-pass filter performing a band-pass process on the original image in a direction that cuts across the grid pattern perpendicularly;

producing a high-pass grid image through high-pass extraction from the original image by performing a high-pass process on the original image, by allowing passage of high frequency components of the grid pattern that are extracted by the high-pass process by the band-pass filter, which is a high-pass filter, in a direction that cuts across the grid pattern perpendicularly;

obtaining a difference between the band-pass grid image and the high-pass grid image, and for producing a difference grid image from the grid frequency components that were not extracted completely in the band-pass through performing a low-pass process, by a low-pass filter, on the difference image, in a direction that is parallel to the grid pattern;

producing separately a band-pass+difference grid image by adding the difference grid image to the band-pass grid image; and obtaining a band-pass+high-pass processed image by subtracting the band-pass+difference grid image from the original image.

* * * * *